US009200029B2

(12) United States Patent
Hashizume et al.

(10) Patent No.: US 9,200,029 B2
(45) Date of Patent: Dec. 1, 2015

(54) PROCESS FOR PRODUCTION OF TRITERPENE ALCOHOL

(75) Inventors: Kohjiro Hashizume, Haga-gun (JP); Takuo Tsuno, Ito-gun (JP); Koji Kato, Ito-gun (JP); Hisahiro Morita, Ito-gun (JP)

(73) Assignees: Kao Corporation, Tokyo (JP); Tsuno Food Industrial Co., Ltd., Wakayama (JP)

(*) Notice: Subject to any disclaimer, the term of this patent is extended or adjusted under 35 U.S.C. 154(b) by 303 days.

(21) Appl. No.: 13/816,778

(22) PCT Filed: Aug. 19, 2011

(86) PCT No.: PCT/JP2011/068737
§ 371 (c)(1),
(2), (4) Date: Feb. 13, 2013

(87) PCT Pub. No.: WO2012/023599
PCT Pub. Date: Feb. 23, 2012

(65) Prior Publication Data
US 2013/0137883 A1    May 30, 2013

(30) Foreign Application Priority Data

Aug. 20, 2010  (JP) ................................. 2010-184676

(51) Int. Cl.
*C07J 53/00*   (2006.01)
*C07J 1/00*    (2006.01)
*C07J 63/00*   (2006.01)
*C11B 3/00*    (2006.01)
*C11C 3/06*    (2006.01)

(52) U.S. Cl.
CPC ................ *C07J 53/004* (2013.01); *C07J 53/00* (2013.01); *C07J 63/008* (2013.01); *C11B 3/006* (2013.01); *C11C 3/06* (2013.01)

(58) Field of Classification Search
USPC ....................................................... 514/510
See application file for complete search history.

(56) References Cited

U.S. PATENT DOCUMENTS

| 5,288,902 | A | | 2/1994 | Taniguchi et al. |
| 5,869,708 | A | * | 2/1999 | Das et al. ...................... 552/510 |
| 7,255,890 | B2 | * | 8/2007 | Sanz Gutierrez ............. 426/656 |
| 7,288,278 | B2 | * | 10/2007 | Mellerup et al. .............. 426/606 |
| 8,048,336 | B2 | * | 11/2011 | Tanabe ........................ 252/299.7 |
| 2003/0165581 | A1 | * | 9/2003 | Wang et al. .................... 424/725 |
| 2003/0195367 | A1 | * | 10/2003 | Barrault et al. ................ 552/540 |
| 2005/0143464 | A1 | * | 6/2005 | Matsuyama et al. .......... 514/559 |
| 2005/0255569 | A1 | * | 11/2005 | Matsuyama et al. .......... 435/127 |
| 2005/0267055 | A1 | * | 12/2005 | Matsuyama et al. ............ 514/33 |
| 2006/0235078 | A1 | * | 10/2006 | Matsuyama et al. .......... 514/548 |
| 2010/0086506 | A1 | | 4/2010 | Tanabe et al. |
| 2011/0212931 | A1 | | 9/2011 | Tanaka et al. |

FOREIGN PATENT DOCUMENTS

| EP | 1 674 089 A1 | 6/2006 |
| EP | 2 377 874 A1 | 10/2011 |
| JP | 51-56442 A | 5/1976 |
| JP | 55-2440 B2 | 1/1980 |
| JP | 5-331101 A | 12/1993 |
| JP | 2001-224309 A | 8/2001 |
| JP | 2004-175679 A | 6/2004 |
| JP | 2006-273764 A | 10/2006 |
| JP | 2010-090206 A | 4/2010 |
| WO | WO 2007/094497 A1 | 8/2007 |
| WO | WO 2010/058795 A1 | 5/2010 |

OTHER PUBLICATIONS

Extended European search report including the supplementary European search report and the European search opinion, for EP Application No. 11818239.3, mailed Mar. 28, 2014, European Patent Office, Munich, Germany.

International Search Report (ISR) for PCT/JP2011/068737; I.A. fd; Aug. 19, 2011, mailed Sep. 13, 2011 from the Japanese Patent Office, Tokyo, Japan.

International Preliminary Report on Patentability (IPRP), Chapter I of the Patent Cooperation Treaty, including the Written Opinion for PCT/JP2011/068737; I.A. fd: Aug. 19, 2011, issued Mar. 19, 2013, from the International Bureau of WIPO, Geneva, Switzerland.

* cited by examiner

*Primary Examiner* — Sabiha N Qazi
(74) *Attorney, Agent, or Firm* — Sterne, Kessler, Goldstein & Fox P.L.L.C.

(57) ABSTRACT

A process for producing triterpene alcohol, comprising sequentially conducting the following steps (A) to (C):
(A) subjecting γ-oryzanol to alkaline hydrolysis;
(B) mixing the alkaline hydrolysate with a low polarity organic solvent, and extracting triterpene alcohol to obtain a triterpene alcohol-containing low polarity organic solvent; and
(C) adding water to the triterpene alcohol-containing low polarity organic solvent thus obtained, removing the low polarity organic solvent, and then melting triterpene alcohol in hot water, followed by cooling.

11 Claims, No Drawings

PROCESS FOR PRODUCTION OF TRITERPENE ALCOHOL

FIELD OF THE INVENTION

The present invention relates to a process for producing triterpene alcohol.

BACKGROUND OF THE INVENTION

Triterpene alcohol is a component of rice bran, olive seeds, corn seeds, aloe and the like, and is the collective name of a series of compounds such as cycloartenol, 24-methylene-cycloartanol, cycloartanol, and cyclobranol. Triterpene alcohol is one of main alcohol components of γ-oryzanol.

In particular, cycloartenol and 24-methylene-cycloartanol are said to have similar physiological actions to γ-oryzanol, and are reported to have the blood cholesterol lowering effect, neutral fat absorption inhibiting effect, and antidiabetic effect.

Triterpene alcohol is produced from the hydrolysate of oryzanol obtained by extracting and recrystallizing deacidified foots, which are formed during the production of rice bran oil or the like. As examples of the method, Patent Document 1 reports the method including subjecting crude oryzanol to alkaline hydrolysis, followed by extraction with acetone and benzene, and then recrystallization and purification with methanol, and Patent Document 2 reports the method including subjecting crude oryzanol to alkaline hydrolysis, followed by precipitation in ice water.

Alternatively, Patent Document 3 reports the method for producing ferulic acid, including subjecting crude oryzanol to alkaline hydrolysis, mixing with hexane, removing the hexane-soluble matter, and then adding dilute sulfuric acid to make the aqueous solution acidic.

CITATION LIST

Patent Document

Patent Document 1: JP-A-55-2440
Patent Document 2: JP-A-2006-273764
Patent Document 3: JP-A-05-331101

SUMMARY OF THE INVENTION

The present invention relates to the following (1) to (13).
(1) A process for producing triterpene alcohol, comprising sequentially conducting the following steps (A) to (C):
(A) subjecting γ-oryzanol to alkaline hydrolysis;
(B) mixing the alkaline hydrolysate with a low polarity organic solvent, and extracting triterpene alcohol to obtain a triterpene alcohol-containing low polarity organic solvent; and
(C) adding water to the triterpene alcohol-containing low polarity organic solvent thus obtained, removing the low polarity organic solvent, and then melting triterpene alcohol in hot water, followed by cooling.
(2) The above process for producing triterpene alcohol, wherein the low polarity organic solvent is hexane.
(3) The above process for producing triterpene alcohol, wherein the amount of water added to the triterpene alcohol-containing low polarity organic solvent is 5 to 100 times by weight of the initial amount of γ-oryzanol.
(4) The above process for producing triterpene alcohol, wherein the amount of water added to the triterpene alcohol-containing low polarity organic solvent is 5 to 20 times by weight of the initial amount of γ-oryzanol.
(5) The above process for producing triterpene alcohol, wherein the amount of water added to the triterpene alcohol-containing low polarity organic solvent is 8 to 15 times by weight of the initial amount of γ-oryzanol.
(6) The above process for producing triterpene alcohol, wherein the temperature of the hot water for melting triterpene alcohol is from 85 to 100° C.
(7) The above process for producing triterpene alcohol, wherein the temperature of the hot water for melting triterpene alcohol is from 90 to 100° C.
(8) The above process for producing triterpene alcohol, comprising conducting adsorption treatment for exposing the triterpene alcohol-containing low polarity organic solvent to an adsorbent before adding water.
(9) The above process for producing triterpene alcohol, wherein the adsorbent is activated carbon.
(10) The above process for producing triterpene alcohol, wherein the amount of the adsorbent used is from 0.1 to 10% by mass with reference to the initial amount of γ-oryzanol.
(11) The above process for producing triterpene alcohol, wherein the amount of the adsorbent used is from 1 to 5% by mass with reference to the initial amount of γ-oryzanol.
(12) The above process for producing triterpene alcohol, wherein the amount of the adsorbent used is from 2 to 5% by mass with reference to the initial amount of γ-oryzanol.
(13) The above process for producing triterpene alcohol, wherein the triterpene alcohol is obtained in the form of granules.

DETAILED DESCRIPTION OF THE INVENTION

The benzene and methanol used in Patent Document 1 are solvents which cannot be used for food use. In addition, it has been found that the purification by recrystallization not only requires great care for the operation of substitution of the solvent, but it also gives a poor yield, and can cause the decrease of the triterpene alcohol content in the product.

The direct recrystallization from the hydrolysate as described in Patent Document 2 leaves residues of ferulic acid, free fatty acids, and alkalis, and thus is unsuitable for obtaining triterpene alcohol with high purity.

Accordingly, the present invention relates to a method for obtaining high purity triterpene alcohol in a high yield.

The inventors carried out dedicated research on the method for extracting triterpene alcohol from crude oryzanol, and have found that triterpene alcohol is produced with high purity and in a high yield by the method including subjecting γ-oryzanol to alkaline hydrolysis, extracting triterpene alcohol with a low polarity organic solvent such as hexane, and then heating and melting triterpene alcohol in water, followed by cooling. The triterpene alcohol crystals obtained by the prior art purification process through recrystallization are difficult to handle. However, the inventors have found that the above-described process provides triterpene alcohol in the form of granules.

The process of the present invention allows the production of high purity triterpene alcohol in a simple procedure and a high yield. In addition, the triterpene alcohol to be obtained is in a granular form and easy to handle. Furthermore, the production process does not use solvents harmful to human bodies, and thus the triterpene alcohol is safe for food use.

In the present invention, the step (A) is alkaline hydrolysis of γ-oryzanol.

γ-Oryzanol is the collective name of ferulates of various triterpene alcohols and phytosterols, and is abundant in deacidified foots (alkaline foots separated in the deacidification process) formed during the production of rice bran oil, rice germ oil, corn oil, and other grain bran oil. γ-Oryzanol may be any of the crude and purified products obtained from the above-described oil. From the viewpoints of easiness of handling and cost, crude crystals of oryzanol which is prepared by extraction from deacidified foots, specifically deacidified foots derived from rice bran oil using a lower alcohol, followed by neutralization, and recrystallization are preferably used. In the crude crystals of oryzanol, the γ-oryzanol content is preferably from 50 to 99% by mass (hereinafter expressed simply as %), and more preferably from 80 to 95%. The γ-oryzanol crude crystals may contain, for example, triglyceride, free fatty acids and the like.

The γ-oryzanol may be a commercially available product.

The alkaline hydrolysis operation may be carried out in accordance with a common procedure. Examples of the alkali include alkali metal hydroxides such as lithium hydroxide, sodium hydroxide, and potassium hydroxide, ammonia, and amines. Among them, from the viewpoint of easiness of handling, alkali metal hydroxides are preferred.

The amount of the alkali used is preferably from 1 to 20 equivalents, and more preferably from 5 to 10 equivalents of the saponification value of γ-oryzanol. The saponification value of γ-oryzanol is measured by, for example, the method described in 2.3.2, Standard Methods for the Analysis of Fats, Oils and Related Materials.

The solvent is not particularly limited as long as it will not inhibit the reaction. Examples of the solvent include water; ethers such as dioxane and tetrahydrofuran; alcohols such as methanol and ethanol; and mixtures of these solvents.

The reaction temperature is not particularly limited, and preferably from 20 to 120° C., and more preferably from 50 to 100° C. The reaction time is preferably from 1 to 50 hours, and more preferably from 5 to 20 hours.

Subsequently, the step (B) is carried out, wherein the alkaline hydrolysate is mixed with a low polarity organic solvent, and triterpene alcohol is extracted to obtain a triterpene alcohol-containing low polarity organic solvent.

The low polarity organic solvent used herein is not particularly limited as long as it is suitable for the extraction of triterpene alcohol. Examples of the low polarity organic solvent include hydrocarbons such as heptane, hexane, and cyclohexane; ketones; and ethers such as diethyl ether, tetrahydrofuran, and dioxane. These solvents may be used alone or in combination of two or more thereof, and may be mixed with water. Among them, heptane and hexane are preferred, and hexane is more preferred, from the viewpoints of use for food or drink use and solubility for triterpene alcohol.

The amount of the low polarity organic solvent to be used may be appropriately established according to the solvent, and preferably from 1 to 100 times, and more preferably from 5 to 20 times by weight of the initial amount of γ-oryzanol.

The temperature of the mixed solution of the alkaline hydrolysate and low polarity organic solvent is preferably from 0 to 80° C., and more preferably from 20 to 65° C. The mixing time is preferably from 1 to 120 minutes, and more preferably from 5 to 60 minutes for achieving sufficient extraction effect.

Subsequently, in a preferred manner, the mixed solution is separated into the solvent layer and aqueous layer, and then the aqueous layer is removed. The aqueous layer containing ferulates, excessive alkalis, and the like is removed by this operation. Triterpene alcohol is extracted into the solvent layer.

Examples of the method for separating the solvent layer and aqueous layer include standing separation and centrifugation. Standing separation is preferably carried out for 10 to 60 minutes, thereby collecting the solvent layer. The temperature during the standing separation is not particularly limited, but preferably from 0 to 80° C., and more preferably from 20 to 65° C. The conditions for centrifugation may be appropriately adjusted according to the separation conditions.

The solvent layer after removal of the aqueous layer is preferably washed several times (for example, two or three times), from the viewpoint of completely removing alkalis. A preferred example of the washing method include mixing the solvent layer with a mixed solvent of a water-soluble organic solvent and water, followed by repeating the removal of the aqueous layer in the same manner as above. Examples of the water-soluble organic solvent include alcohols. Among them, ethanol is preferred from the viewpoint of use for food or drink.

Subsequently, the step (C) is carried out. In the step (C), water is added to the triterpene alcohol-containing low polarity organic solvent, the low polarity organic solvent is removed, and then triterpene alcohol is melted in hot water, followed by cooling.

The amount of water is 5 to 100 times, preferably 5 to 20 times, and more preferably 8 to 15 times by weight of the initial amount of γ-oryzanol, from the viewpoint of handling after removal of the low polarity organic solvent. Examples of water include tap water, purified water, distilled water, and deionized water.

The method of the removal of the low polarity organic solvent depends on the type and composition of the solvent, but preferably, for example, evaporation is carried out at a temperature of 30 to 150° C., preferably 40 to 90° C., and more preferably 70 to 80° C. The pressure may be reduced pressure or normal pressure. At this time, it is preferred that the evaporation be continued until the removed amount of the low polarity organic solvent becomes equal to the amount of the solvent to be used in the step (B).

After removal of the low polarity organic solvent, triterpene alcohol is melted in hot water. The temperature of the hot water at this time is not particularly limited as long as the temperature is not lower than the melting point of triterpene alcohol. The temperature is preferably from 85 to 100° C., and more preferably from 90 to 100° C. The melting operation is preferably carried out under stirring at a stirring rate of 200 to 450 r/min, preferably 250 to 400 r/min, and more preferably 300 to 400 r/min from the viewpoints of dispersing the melted triterpene alcohol and preventing flocculation. The melted and dispersed states can be confirmed by, for example, visual observation.

After melting triterpene alcohol, the temperature is decreased to 20 to 84° C., and preferably 40 to 60° C. As a result of this, triterpene alcohol solidifies into granules in water, and triterpene alcohol is obtained in the form of granules by, for example, filtrating the solution.

In the present invention, adsorption treatment for contacting the triterpene alcohol-containing low polarity organic solvent with an adsorbent may be carried out before the step (C). As a result of this, coloring of the final product of triterpene alcohol is reduced.

The adsorbent used herein is preferably a porous adsorbent, and examples thereof include activated carbon, silicon dioxide, and solid acid adsorbent. Examples of the solid acid adsorbent include acid clay, activated clay, active alumina, silica gel, silica-alumina, and aluminum silicate. These adsorbents may be used alone or in combination of two or more thereof. Among them, activated carbon is preferred from the viewpoints of bleaching effect and prevention of side reactions.

When activated carbon is used as the adsorbent, the amount of it used is preferably from 0.1 to 10%, more preferably from 1 to 5%, and even more preferably from 2 to 5%, with reference to the initial amount of γ-oryzanol.

The temperature during the contact between the triterpene alcohol-containing low polarity organic solvent and adsorbent is preferably from 20 to 100° C., and more preferably from 20 to 40° C. for achieving good bleaching performance. The contact time is, from the same viewpoint, preferably from 3 to 90 minutes, more preferably from 15 to 90 minutes, and even more preferably from 30 to 50 minutes. The pressure may be reduced or normal pressure.

The granular triterpene alcohol obtained in the step (C) is preferably densified to form, for example, a dehydrated concentrate or a dry solid or powder. Examples of the densification method by concentration or drying include vacuum concentration, spray drying, and freeze drying.

The triterpene alcohol of the present invention thus obtained has high purity because it contains no ferulic acid, free fatty acids, alkali and the like, and offers a wide range of applications due to the easiness of handling. For example, the triterpene alcohol of the present invention may be added to various beverages and foods.

EXAMPLES

Analysis of Triterpene Alcohol

About 25 mg of the sample was taken, and chloroform was added to make the volume 10 mL. 1 μL of the solution was injected into GC, and analyzed. The GC analysis conditions are described below. The quantification values of cycloartenol and 24-methylene-cyclocycloartanol were determined by absolute quantification using calibration curves which had been constructed using purified products of these components (prepared at Kao Corporation).

Column: Capillary GC column DB-1 (J&W), 30 m×0.25 mm, film thickness 0.25 μm
Carrier gas: He, 2.30 mL/min
Injector: Split (40:1), T=300° C.
Detector: FID, T=300° C.
Oven temperature: kept at 150° C. for 1.5 minutes, increased to 250° C. at 15° C./minute, increased to 320° C. at 5° C./minute, and kept for 3 minutes Example 1

50 g of γ-oryzanol (Tsuno Co., Ltd., purity: 89.2%, saponification value: 103) was mixed with 250 mL of 2 N potassium hydroxide-90 v/v % aqueous ethanol solution, and stirred for 6 hours under reflux in a nitrogen atmosphere.

After confirming the completion of the hydrolysis reaction, the temperature was allowed to decrease to 55° C., and 500 mL of n-hexane and 200 mL of water were added thereby extracting the triterpene alcohol thus formed. The mixture was stirred for 20 minutes with keeping the temperature at 55° C., allowed to stand until the layers separated (20 minutes), and the separated aqueous layer was removed. 250 mL of 60 v/v % aqueous ethanol solution was added to the hexane layer, and stirred again for 20 minutes with keeping the temperature at 55° C. After the mixture was allowed to stand until the layers separated (20 minutes), the separated aqueous layer was removed. 250 mL of 60 v/v % aqueous ethanol solution was further added to the hexane layer, and stirred again for 20 minutes with keeping the temperature at 55° C. After the mixture was allowed to stand until the layers separated (20 minutes), the separated aqueous layer was removed. As a result of this procedure, the pH of the aqueous layer decreased to 7, indicating that the alkali used for the reaction was thoroughly removed from the hexane layer by water washing.

400 mL of water was added to the remnant hexane layer, heated at 70 to 80° C. under normal pressure, thereby evaporating hexane. When the amount of evaporated hexane reached about 500 mL, the temperature of the remnant triterpene alcohol suspension was increased (90 to 100° C.), and the triterpene alcohol was melted and dispersed under stirring at 300 to 400 r/min. Heating was stopped when the melting and dispersion of triterpene alcohol were confirmed, and the temperature was allowed to decrease to 50° C. At that time, the melted triterpene alcohol was solidified into granules, with dispersed in water.

The granular triterpene alcohol thus obtained was collected by filtration, washed with 100 mL of water, and then vacuum-dried (50° C., 15 hours), thereby obtaining 30 g of powdery triterpene alcohol (yield: 94%). Table 1 shows the result of analysis of the components of this product by capillary gas chromatography.

Example 2

In the same manner as in Example 1, γ-oryzanol was hydrolyzed, and triterpene alcohol thus formed was extracted with hexane and washed with water.

1 g of activated carbon (CARBORAFIN, Japan Enviro-Chemicals. Ltd) was added to the hexane layer thus obtained, and stirred for 30 minutes at room temperature.

The activated carbon was removed by filtration, 400 mL of water was added to the remnant hexane solution, and the same procedure as in Example 1 was carried out, thereby obtaining 30 g of powdery triterpene alcohol (yield: 94%). Table 1 shows the result of analysis of the components of this product by capillary gas chromatography.

Comparative Example 1

In the same manner as in Example 1, γ-oryzanol was hydrolyzed, and triterpene alcohol thus formed was extracted with hexane and washed with water.

Hexane was evaporated from the hexane layer thus obtained under reduced pressure, and thus obtaining 34 g of a dry solid of triterpene alcohol. 340 mL of 85 v/v % aqueous ethanol solution was added to the dry solid of triterpene alcohol, the mixture was heated to 70° C., thereby completely dissolving the dry solid. Thereafter, the temperature was decreased to room temperature over a period of 30 minutes, and recrystallization was carried out at 25° C. for 2 hours. The precipitated crystals were collected by filtration, the crystals were further washed with 60 mL of 85 v/v % aqueous ethanol solution, and vacuum-dried (50° C., 15 hours), thereby obtaining 25 g of triterpene alcohol in the form of a slightly viscous wax (yield: 78%). Table 1 shows the result of analysis of the components of this product by capillary gas chromatography.

TABLE 1

| | Example 1 | Example 2 | Comparative Example 1 |
|---|---|---|---|
| Appearance | Pale yellow granular powder | White granular powder | Viscous wax |
| Yield | 94% | 94% | 78% |
| Total of GC detected peaks (total sterol content) | 92% | 90% | 79% |

TABLE 1-continued

|  | Example 1 | Example 2 | Comparative Example 1 |
|---|---|---|---|
| Cycloartenol (quantification value) | 26% | 25% | 19% |
| 24-methylene-cycloartanol (quantification value) | 37% | 37% | 32% |

As is evident from Table 1, the method of the present invention provided high purity triterpene alcohol with a high recovery rate as much as 945 (Examples 1 and 2). On the other hand, when crystallizing purification was carried out after hexane extraction, the yield of triterpene alcohol was low, the cycloartenol content in triterpene alcohol was low, and the purity was also low (Comparative Example 1).

What is claimed is:

1. A process for producing triterpene alcohol in the form of granules, comprising sequentially conducting the following steps (A) to (C):
   (A) subjecting γ-oryzanol to alkaline hydrolysis;
   (B) mixing the alkaline hydrolysate with a low polarity organic solvent, and extracting triterpene alcohol to obtain a triterpene alcohol-containing low polarity organic solvent; and
   (C) adding water to the triterpene alcohol-containing low polarity organic solvent thus obtained, removing the low polarity organic solvent, and then melting triterpene alcohol in hot water, wherein the temperature of the hot water for melting the triterpene alcohol is from 85 to 100° C., followed by cooling, wherein the triterpene alcohol is obtained in the form of granules.

2. The process for producing triterpene alcohol according to claim 1, wherein the low polarity organic solvent is hexane.

3. The process for producing triterpene alcohol according to claim 1, wherein the amount of water added to the triterpene alcohol-containing low polarity organic solvent is 5 to 100 times by weight of the initial amount of γ-oryzanol.

4. The process for producing triterpene alcohol according to claim 1, wherein the amount of water added to the triterpene alcohol-containing low polarity organic solvent is 5 to 20 times by weight of the initial amount of γ-oryzanol.

5. The process for producing triterpene alcohol according to claim 1, wherein the amount of water added to the triterpene alcohol-containing low polarity organic solvent is 8 to 15 times by weight of the initial amount of γ-oryzanol.

6. The process for producing triterpene alcohol according to claim 1, wherein the temperature of the hot water for melting triterpene alcohol is from 90 to 100° C.

7. The process for producing triterpene alcohol according to claim 1, comprising conducting adsorption treatment for exposing the triterpene alcohol-containing low polarity organic solvent to an adsorbent before adding water.

8. The process for producing triterpene alcohol according to claim 7, wherein the adsorbent is activated carbon.

9. The process for producing triterpene alcohol according to claim 7, wherein the amount of the adsorbent used is from 0.1 to 10% by mass with reference to the initial amount of γ-oryzanol.

10. The process for producing triterpene alcohol according to claim 7, wherein the amount of the adsorbent used is from 1 to 5% by mass with reference to the initial amount of γ-oryzanol.

11. The process for producing triterpene alcohol according to claim 7, wherein the amount of the adsorbent used is from 2 to 5% by mass with reference to the initial amount of γ-oryzanol.

* * * * *